(12) United States Patent
Durand et al.

(10) Patent No.: US 11,331,026 B2
(45) Date of Patent: May 17, 2022

(54) INTERFACING WITH THE PERIPHERAL NERVOUS SYSTEM (PNS) USING TARGETED FASCICULAR INTERFACE DEVICE

(71) Applicant: Case Western Reserve University, Cleveland, OH (US)

(72) Inventors: Dominique Durand, Cleveland, OH (US); Grant McCallum, Cleveland, OH (US); Chen Qiu, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 412 days.

(21) Appl. No.: 16/401,152

(22) Filed: May 2, 2019

(65) Prior Publication Data
US 2019/0254547 A1 Aug. 22, 2019

Related U.S. Application Data

(62) Division of application No. 14/537,944, filed on Nov. 11, 2014, now abandoned.
(Continued)

(51) Int. Cl.
*A61N 1/05* (2006.01)
*A61B 5/24* (2021.01)

(52) U.S. Cl.
CPC .............. *A61B 5/24* (2021.01); *A61N 1/0558* (2013.01); *A61N 1/0556* (2013.01)

(58) Field of Classification Search
CPC ............................ A61N 1/0558; A61N 1/0556
See application file for complete search history.

(56) References Cited

U.S. PATENT DOCUMENTS

| 4,000,745 A * | 1/1977 | Goldberg ............. A61N 1/0587 607/127 |
| 4,711,243 A | 12/1987 | Schafer |

(Continued)

OTHER PUBLICATIONS

S. V. Conde, E. C. Monteiro, R. Rigual, A. Obeso, and C. Gonzalez, "Hypoxic intensity: a determinant for the contribution of ATP and adenosine to the genesis of carotid body chemosensory activity", Journal of Applied Physiology 2012 112:12, 2002-2010 (Year: 2012).*

(Continued)

*Primary Examiner* — William J Levicky
(74) *Attorney, Agent, or Firm* — Tarolli, Sundheim, Covell & Tummino LLP

(57) ABSTRACT

A stealthy conductor that may be placed inside a fascicle in the peripheral nervous system (PNS) is described. The conductor is placed using a targeted-fascicle or targeted-axon approach to improve specificity and signal to noise ratio (SNR). The conductor is part of a targeted fascicular interface device and is placed using an insertion tool in a manner that reduces nerve damage as compared to conventional systems. The conductor is so small (e.g., <10 μm diameter) and so flexible (e.g., approximates flexibility of surrounding neuronal material) that biological reactions (e.g., recruitment of macrophages, edema) to the presence of the conductor may be reduced. The targeted fascicular interface device has an insulated portion and a non-insulated portion that may act as an electrode. The insulated portion may include materials that promote healing at the entry/exit site and that adhere to the perineurium.

12 Claims, 15 Drawing Sheets

Related U.S. Application Data

(60) Provisional application No. 61/905,094, filed on Nov. 15, 2013.

(56) References Cited

U.S. PATENT DOCUMENTS

| | | | | |
|---|---|---|---|---|
| 5,173,295 | A * | 12/1992 | Wehling | A61L 24/0015 424/94.67 |
| 5,324,322 | A * | 6/1994 | Grill, Jr. | A61N 1/0556 600/375 |
| 5,400,784 | A | 3/1995 | Durand et al. | |
| 5,834,029 | A * | 11/1998 | Bellamkonda | A61L 27/20 606/152 |
| 6,405,079 | B1 * | 6/2002 | Ansarinia | A61N 1/36071 607/2 |
| 2004/0199235 | A1 * | 10/2004 | Younis | A61N 1/0539 607/116 |
| 2005/0177201 | A1 * | 8/2005 | Freeman | A61N 1/0529 607/46 |
| 2010/0211172 | A1 * | 8/2010 | Bellamkonda | A61N 1/0556 607/116 |
| 2010/0268055 | A1 * | 10/2010 | Jung | A61N 1/0558 600/377 |
| 2011/0168288 | A1 | 7/2011 | Axelrad et al. | |
| 2013/0110212 | A1 * | 5/2013 | Feng | A61N 1/056 607/119 |
| 2013/0110213 | A1 | 5/2013 | Feng et al. | |

OTHER PUBLICATIONS

Malmstrom et al, "Recording Properties and Biocompatibility of Chronically Implanted Polymer-based Intrafascicular Electrodes", Annals of Biomedical Engineering vol. 26 (Issue.6), pp. 1055-1064 (Year: 1998).*

Boretius, Tim, et al. "A transverse intrafascicular multichannel electrode (TIME) to interface with the peripheral nerve." Biosensors and Bioelectronics 26.1 (2010): 62-69.

Branner, Almut, R. B. Stein, and R. A. Normann. "Selective stimulation and recording using a slanted multielectrode array." Proceedings of the First Joint BMES/EMBS Conference. 1999 IEEE Engineering in Medicine and Biology 21st Annual Conference and the 1999 Annual Fall Meeting of the Biomedical Engineering Society (Cat. N. vol. 1. IEEE, 1999.

Lago, Natalia, et al. "Assessment of biocompatibility of chronically implanted polyimide and platinum intrafascicular electrodes." IEEE Transactions on Biomedical Engineering 54.2 (2007): 281-290.

Navarro, Xavier, et al. "A critical review of interfaces with the peripheral nervous system for the control of neuroprostheses and hybrid bionic systems." Journal of the Peripheral Nervous System 10.3 (2005): 229-258.

Stoll, Guido, and Hans Werner Muller. "Nerve injury, axonal degeneration and neural regeneration: basic insights." Brain pathology 9.2 (1999): 313-325.

Yoshida, Ken, and Ken Horch. "Selective stimulation of peripheral nerve fibers using dual intrafascicular electrodes." IEEE transactions on biomedical engineering 40.5 (1993): 492-494.

* cited by examiner

INTERFACING WITH THE PERIPHERAL NERVOUS SYSTEM (PNS) USING TARGETED FASCICULAR INTERFACE DEVICE

CROSS REFERENCE TO RELATED APPLICATIONS

This application is a Divisional of U.S. patent application Ser. No. 14/537,944, filed Nov. 11, 2014, which claims the benefit of U.S. Provisional Application Ser. No. 61/905,094, filed Nov. 15, 2013. Each of which is hereby incorporated by reference for all purposes.

BACKGROUND

While the field of neural prosthetics continues to grow, viable applications have been limited due to the lack of an adequate interface with the nervous system. Goals for neural interfaces include improving selectivity, improving signal to noise ratio (SNR), and improving durability all while lowering damage to the nerve with which the interface interacts. Attempts to produce an adequate interface have faced biological, mechanical, or electrical problems where the peripheral nerve and the man-made electrodes interact. Various approaches using different strategies have been attempted for interfacing with nerve fibers. The various approaches differ in invasiveness, selectivity, angle or plane of interface, the number of holes made in a nerve, materials used, and in other factors. The various approaches include cuff designs, intrafascicular designs, shaft designs, regenerative electrodes, and others. See, for example, Navarro et al., A critical review of interfaces with the peripheral nervous system for the control of neuroprostheses and hybrid bionic systems, J. Periph. Nerv. System, vol. 10, pp 229-258, 2005.

FIG. 1 illustrates a nerve 100 in the peripheral nervous system (PNS). In nerve 100, nerve fibers are each wrapped in a protective sheath known as the endoneurium 110. The nerve fibers are bundled together into groups known as fascicles. A fascicle 140 is surrounded by a protective sheath called the perineurium 120. Several fascicles may be bundled together with a blood supply 150 and fatty tissue within another sheath called the epineurium 130. The epineurium 130 may be relatively easy to breach during surgery compared to the perineurium 120. A nerve fascicle may include an axon 160.

FIG. 2 illustrates another view of a nerve 200. The perineurium 210 is composed of very tough connective tissue that has a lamellar arrangement consisting of roughly 7-8 concentric layers. The perineurium 210 is composed of perineurial cells, which are epithelioid myofibroblasts. Perineurial cells are sometimes referred to as myoepithelioid due to their epithelioid and myofibroblastoid properties including tight junctions, gap junctions, external laminae and contractility. The perineurium 210 is a smooth, transparent tubular membrane that can be separated from the fibers it encloses but is difficult to penetrate. In contrast, the epineurium 220 is made up mostly of collagen and is easier to penetrate. In conventional systems, an electrode may penetrate the epineurium 220 but when the electrode comes in contact with the perineurium 210 of a fascicle it may be deflected or push the fascicle aside and thus may not actually penetrate the fascicle.

Some conventional attempts to interface with the PNS surround a nerve with a multi-contact cuff electrode placed outside the epineurium that provides a stable and safe interface. However, the external multi-contact cuff electrode that surrounds the nerve and all of its fascicles and thus all of its axons may have a low SNR for recording signals because the signals from an axon may be mixed with signals from other axons and because the signal will have to transit both the endoneurium, the perineurium and the epineurium. Additionally, the multi-contact cuff may have low selectivity with respect to any specific fascicle or any specific axon.

Other conventional approaches penetrate both the epineurium and the perineurium using relatively large and stiff electrodes that can improve the SNR over an electrode that does not penetrate the nerve. The penetration may be unguided and therefore individual fascicles may not be targeted. Some fascicles may only be partially penetrated, which may potentially cause significant damage while providing suboptimal access to an individual fascicle or axon. An unguided technique may result in an electrode being placed in a fascicle or may equally likely result in an electrode not being placed in a fascicle. An unguided approach may result in an electrode placed partially inside a fascicle but with no immediate, verifiable feedback.

Conventional approaches have not demonstrated long term stability. For example, wires or electrodes placed by conventional approaches may have moved around due to forces experienced by the wire (e.g., tethering force, shear force).

Conventional approaches for interfacing with the PNS include the Utah Electrode Array (UEA) and the Utah Slant Electrode Array (USEA) which are designed to record/stimulate many neurons simultaneously. See, for example, Branner et al., 1999, Selective stimulation and recording using a slanted multielectrode array, IEEE Engineering in Medicine and Biology $21^{st}$ Annual Conf. and the Annual Fall Meeting of the Biomedical Engineer Society (Atlanta, Ga., USA). FIG. 3 illustrates an example USEA 300. This approach punctures the epineurium of a nerve at multiple locations and potentially punctures the perineurium of several fascicles at multiple locations using multiple electrodes that end up perpendicular or substantially perpendicular to the nerve that is punctured in the multiple locations. The amount of damage associated with application of USEA 300 may be significant. The electrodes in USEA 300 may be rigid, and thus any relative motion between the penetrated nerve and the device may cause additional damage.

FIG. 4 illustrates an example of a cuff approach 400, a TIME approach 420, and a LIFE approach 410. In cuff approach 400, a nerve 404 is surrounded by a cuff 402 to which a cable 406 is attached. The cuff approach 400 tends to produce an area of activation 408 near the outside of nerve 404. The LIFE approach 410 introduces a cable 416 into nerve 412 with the hope of entering a fascicle 414. The TIME approach 420 introduces a cable 422 perpendicularly into nerve 424 with the hope of interacting with one or more fascicles.

One experimental approach for interfacing with the PNS is the Transverse Intrafascicular Multichannel Electrode (TIME) approach. See, for example, A transverse intrafascicular multichannel electrode to interface with the peripheral nerve, Boretius et al., Biosensors and Bioelectronics 26 (2010) 62-69. The TIME approach includes an electrode design that transversally penetrates the peripheral nerve and that is intended to selectively activate subsets of axons in different fascicles within the nerve. FIG. 5 illustrates how a TIME cable 506 is inserted into a nerve 504. Note that there will be both an entry wound and an exit wound. At time 500, an insertion tool 502 punctures the nerve 504. The insertion tool 502 is attached to a TIME cable 506. At time 510, the insertion tool 502 has punctured both sides of nerve 504. At time 520, the insertion tool 502 has exited the nerve 504 and is pulling the TIME cable 506 into the nerve 504. At time 530, the TIME cable 506 has been pulled through nerve 504 and has one side exposed on one side of nerve 504 and has another side exposed on the other side of nerve 504. The TIME approach may make it difficult, if even possible at all, to target specific fascicles.

Another experimental approach for interfacing with the PNS is the longitudinal intrafascicular electrode (LIFE). See, for example, Yoshida et al., Selective stimulation of peripheral nerve fibers using intrafascicular electrodes, IEEE Trans. Biomed Eng., vol. 40, no. 5, pp 492-494, May 1993. FIG. 6 illustrates a LIFE electrode 620 being pulled through a nerve 640 by a cable 630. At time 600, the cable 630 is advanced though nerve 640. At time 610, the cable 630 has exited nerve 640 but is still used to pull electrode 620 through the nerve 640. There is an entry point and an exit point. The cable 630 may be a needle (e.g., electro sharpened tungsten needle measuring 80 µm in diameter). The LIFE electrode 620 may be sutured to the epineurium at both the entry point and exit point.

LIFE electrodes have been constructed from PT or PT-IR wire and from polyimides. The PT wire may have been insulated with Teflon. For PT wire embodiments, the stiffness of the electrode structure is dominated by the conductor PT-IR core and has a Young's Modulus of 202 GPa. For PT wire embodiments, the electrodes may have had an effective outer diameter of 60-75 µm. Polyimide embodiments may have a Young's Modulus of 8.3 GPa and when fashioned into a ribbon configuration have a width of 160 µm. LIFE electrodes may have produced sub-optimal results due, for example, to continued motion of a LIFE electrode within a fascicle. Additionally, LIFE electrodes may have produced a mild functional decline after implantation due to damage induced during surgery and subsequent injury effects due to mechanical motion and compression induced by the electrode inside the nerve. The LIFE electrode may have produced a focal axonal conduction block due to increased pressure exerted by the electrode within the endoneurium. The continued relative motion of the electrode within the fascicle may have caused both a gradual drift in the recorded nerve fiber population and a reduction of SNR. See, for example, Lago, et al., Assessment of Biocompatibility of Chronically Implanted Polyimide and Platinum Intrafascicular Electrodes.

Macrophages are heavily recruited to enter damaged peripheral nerves. See, for example, Stoll, et al., Nerve injury, axonal degeneration and neuronal regeneration basic insights, Brain Pathol., vol. 9, pp. 313-325, 1999. Multiple entry sites for the USAE may provide multiple wound sites to which macrophages are recruited. For both the LIFE and TIME approaches, the entry and exit sites for the needle insertion approach provide at least two wound sites to which macrophages are recruited. Also, having both an entry and exit site produces at least two locations where mechanical strain may be placed on an implanted electrode and where the nerve brain barrier may be compromised

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example apparatus and methods concern one or more stealthy conductors (e.g., micro-wires, nanowires, nanotube assemblies) that may be placed longitudinally inside a fascicle in the peripheral nervous system (PNS) using a single entry point. In different embodiments the stealthy conductor may be placed longitudinally, diagonally, or perpendicularly. In one embodiment, the stealthy conductor may be placed through a single entry point, while in another embodiment the stealthy conductor may be placed using both an entry point and an exit point. A stealthy biocompatible conductor may be placed using a targeted-fascicle or targeted-axon approach. The conductor is placed using an insertion tool in a manner that reduces nerve damage as compared to conventional systems. Additionally, the conductor is so small (e.g., <10 µm diameter) and so flexible (e.g., approximates flexibility of surrounding neuronal material) that the body or nerve may not react to the presence of the conductor. Reducing reactions (e.g., recruitment of macrophages, edema) to the presence of the conductor may provide improvements over conventional systems that place larger electrodes using approaches that produce more nerve damage.

Figure 1:
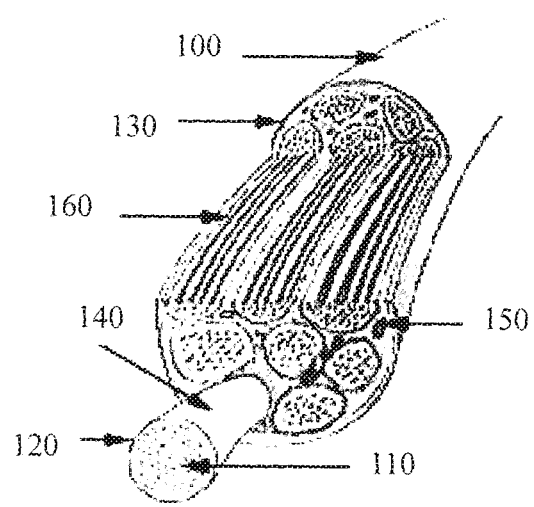
FIG. 1 illustrates a nerve.
Figure 2:
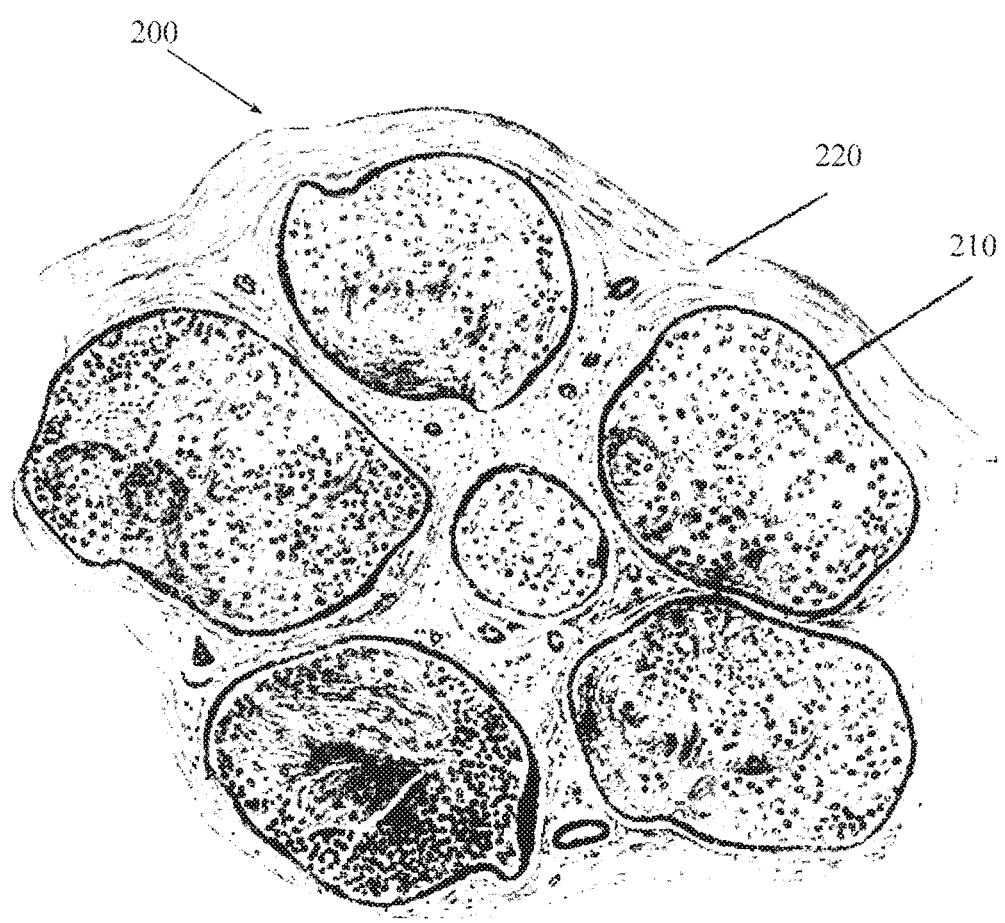
FIG. 2 illustrates a nerve.
Figure 3:
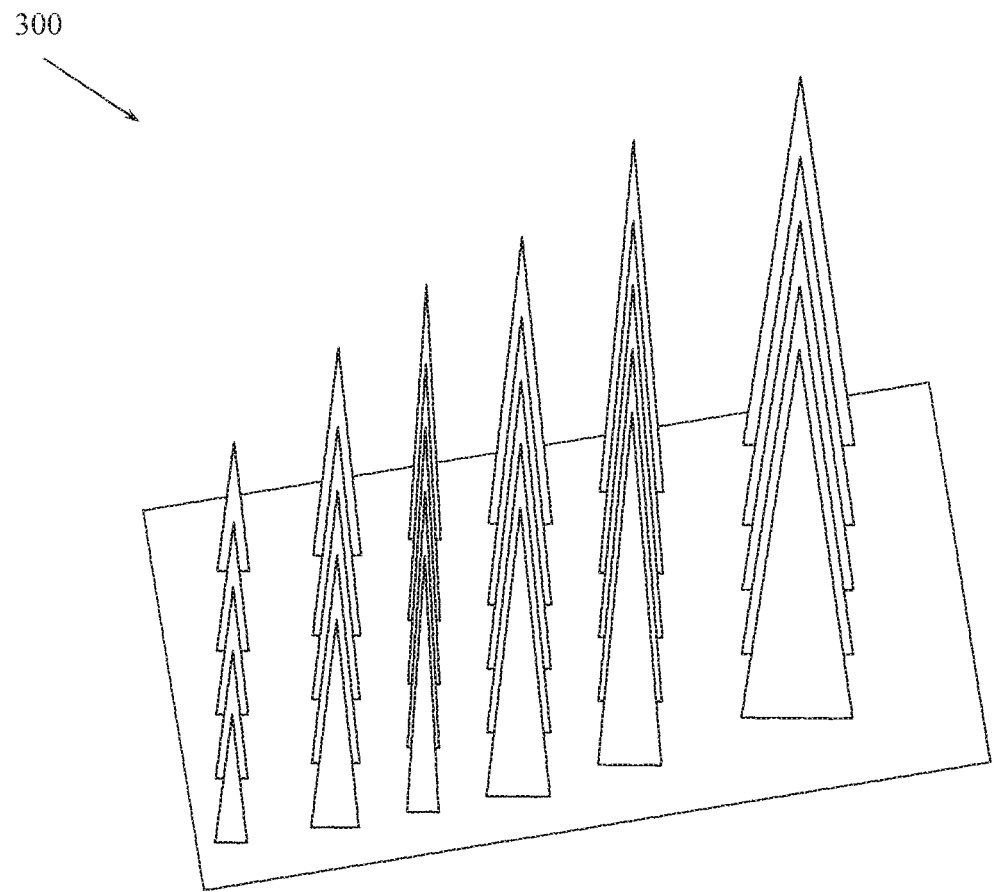
FIG. 3 illustrates a Utah Slant Array Electrode.
Figure 4:
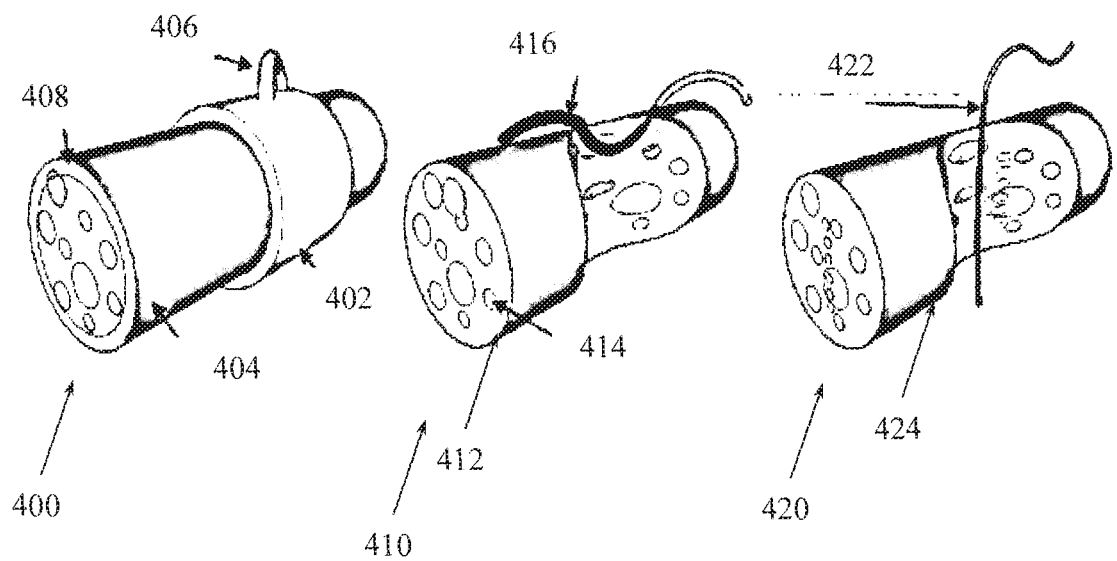
FIG. 4 illustrates various approaches for interfacing with a nerve.
Figure 5:
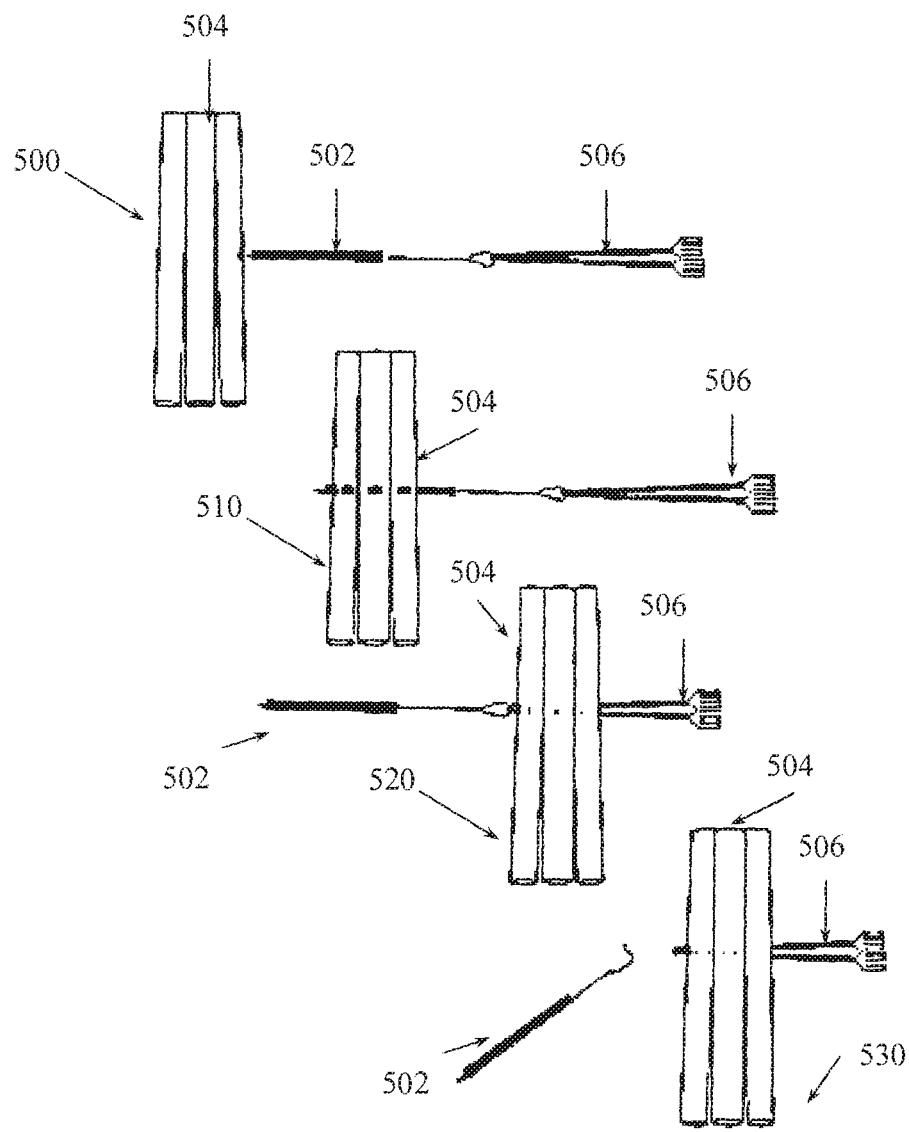
FIG. 5 illustrates a TIME approach for interfacing with a nerve.
Figure 6:
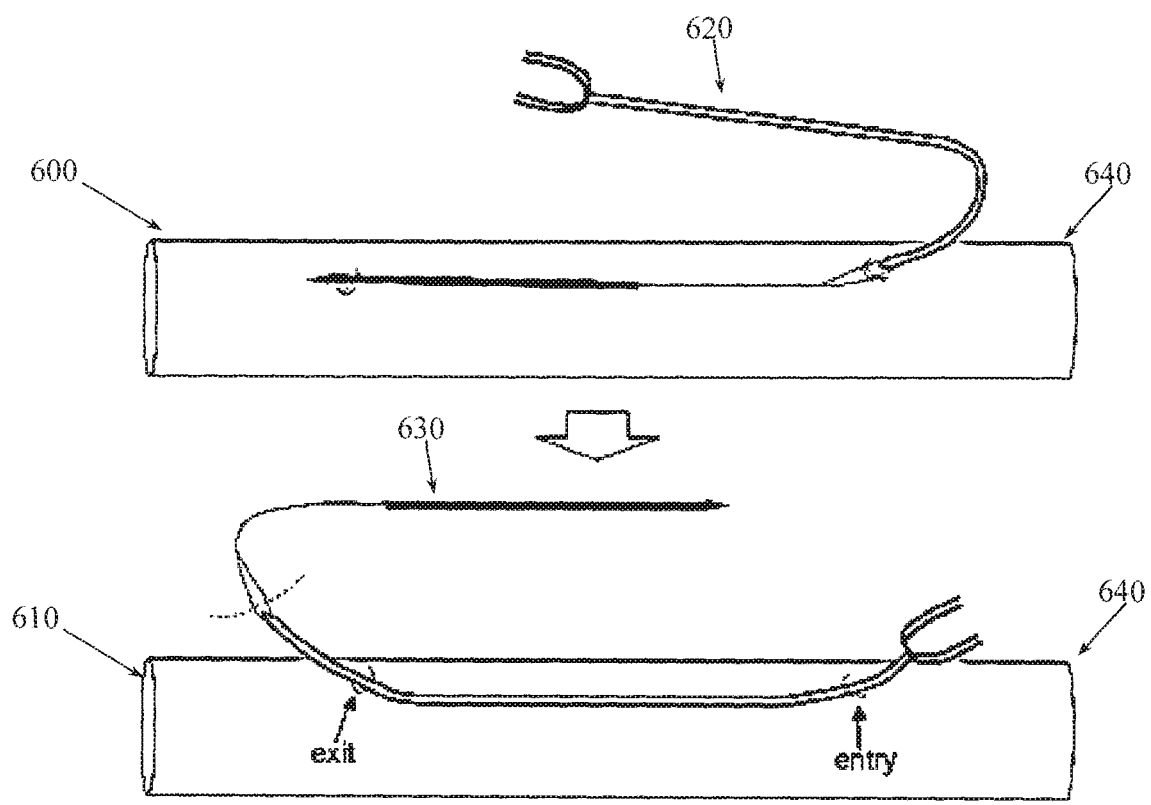
FIG. 6 illustrates a LIFE approach for interfacing with a nerve.
Figure 7:
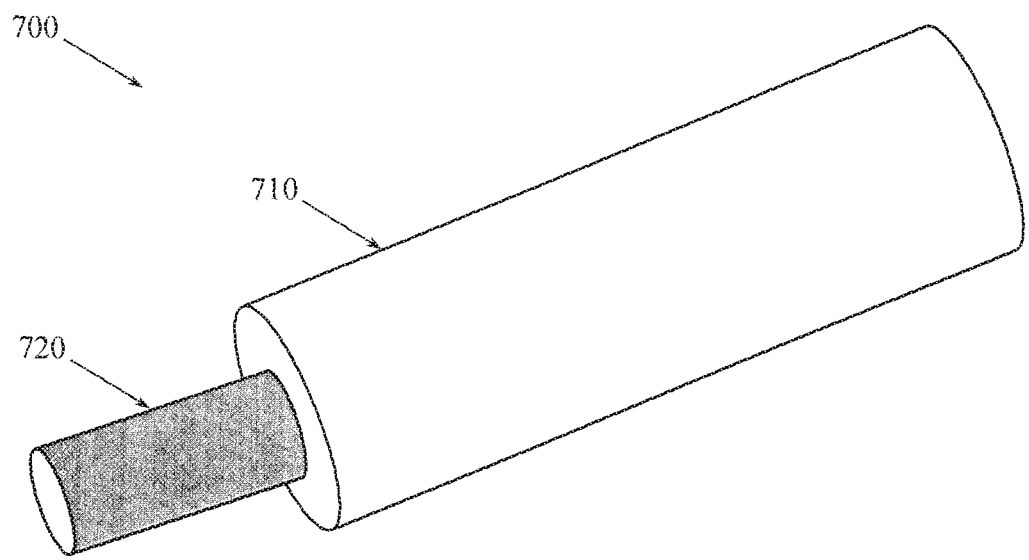
FIG. 7 illustrates a device for interfacing with a selected axon inside a single fascicle in a nerve in the PNS using a single hole in the epineurium of the nerve and a single hole in the perineurium of the fascicle.

FIG. 7 illustrates an example targeted fascicular interface device 700 that includes an insulated portion 710 and a non-insulated conducting portion 720 that may act as an electrode. The conductor 720 is a biocompatible conductor that receives an electrical signal from one or several axons or provides an electrical stimulation to the axon while positioned longitudinally within a threshold distance of the axon for at least a run length. The conductor 720 may be, for example, a platinum wire, a carbon nanotube, or other electrically conducting material. In one embodiment, the conductor 720 has a diameter of less than 11 μm, and has a flexural rigidity similar to that of nerves (e.g., $144 \times 10^{-9}$ Pa*m$^2$). Flexural rigidity is the product of an object's Young's Modulus and the second moment of inertia about an axis. The insulator 710 covers at least a portion of the conductor 720.

Making the conductor 720 as small as possible while still supporting signal conduction facilitates reducing or minimizing damage to the nerve. The conductor 720 may also be flexible enough to improve or even maximize mechanical compatibility with the nerve. The conductor 720 may also be flexible enough to provide strain relief. The conductor 720 may have properties (e.g., size, flexibility) that mimic the properties of surrounding neuronal material. Having the conductor 720 match the flexibility or other properties of the surrounding neuronal material may reduce the likelihood of micro motion issues, which may in turn make the conductor 720 so stealthy that biological responses (e.g., immune response, edema) are reduced as compared to conventional systems. The likelihood of micro motion issues may be reduced because the conductor may move with the nerve rather than being a rigid fixed object against which the nerve strains.

The insulator 710 may be made from a material that promotes healing at the single hole in the perineurium, and a material that adheres to the perineurium. The insulator 710 may be selected to promote healing at a location where the targeted fascicular interface device enters the fascicle through the perineurium. The promoted healing may facilitate holding the targeted fascicular interface device in place after surgery, which may resolve issues with conventional systems. An example targeted fascicular interface device may be positioned so that the conductor 720 is in contact with the edges of the hole in the perineurium. The insulator 710 in contact with the perineurium may be, for example, titanium, parylene-C or Teflon or another material that facilitates cell adhesion to the implanted structure. Perineurium cells originate from fibroblasts and fibroblasts have been shown to adhere well to parylene-C. In one embodiment, the insulator 710 may be coated with a thin layer of titanium or collagen or other substance to improve cell adhesion. In one embodiment, the insulator 710 may be amorphous carbon with a purity of at least 99%. In one embodiment, the insulator may be Silicone (e.g., siloxanes, Polydimethylsiloxane).

Rather than blindly placing a targeted fascicular interface device, example methods expose the target fascicle and visually guide the targeted fascicular interface device 700 to the intended destination. The placement of the targeted fascicular interface device 700 may be tested before the implantation procedure is complete. In one embodiment, the targeted fascicular interface device 700 may be placed longitudinally or in the same plane as a desired fascicle or axon so that the conductor 720 stays within a threshold distance of the desired axon for a certain run length. The threshold distance may be, for example, 100 μm. The run length, which is the length over which the threshold distance is maintained, may be, for example, 1 mm. While the targeted fascicular interface device 700 may be positioned longitudinally alongside the neural signal conductor, other orientations are possible.

In different embodiments the targeted fascicular interface device may be cylindrical or may be non-cylindrical. In one embodiment, the conductor may include several micro-wires, nano-wires, or nano-structures. The nano-structures may be, for example, carbon nanotubes.

Example apparatus and methods provide a reliable interface between a peripheral nerve and an implanted electronic interface. In one embodiment, the interface may be configured for fascicle-selective stimulation, fascicle-selective recording, or fascicle-selective stimulation and recording. In one embodiment, the interface may be configured for axon-selective stimulation, axon-selective recording, or axon-selective stimulation and recording. In different embodiments, the interface may be applied to different fascicles or axons to facilitate separately detecting sensory activity and motor activity. Fascicle selective operation or axon selective operation may be enhanced by a targeted approach that places the conductor within a threshold distance of a neural signal conductor (e.g., nerve fiber) for a threshold run length inside a fascicle. Placing the conductor alongside or in the same plane as the neural signal conductor may provide improved SNR over a wire that is placed perpendicular to the neural signal conductor. While the conductor may be positioned longitudinally alongside the neural signal conductor in some embodiments other orientations are possible.

Figure 8:
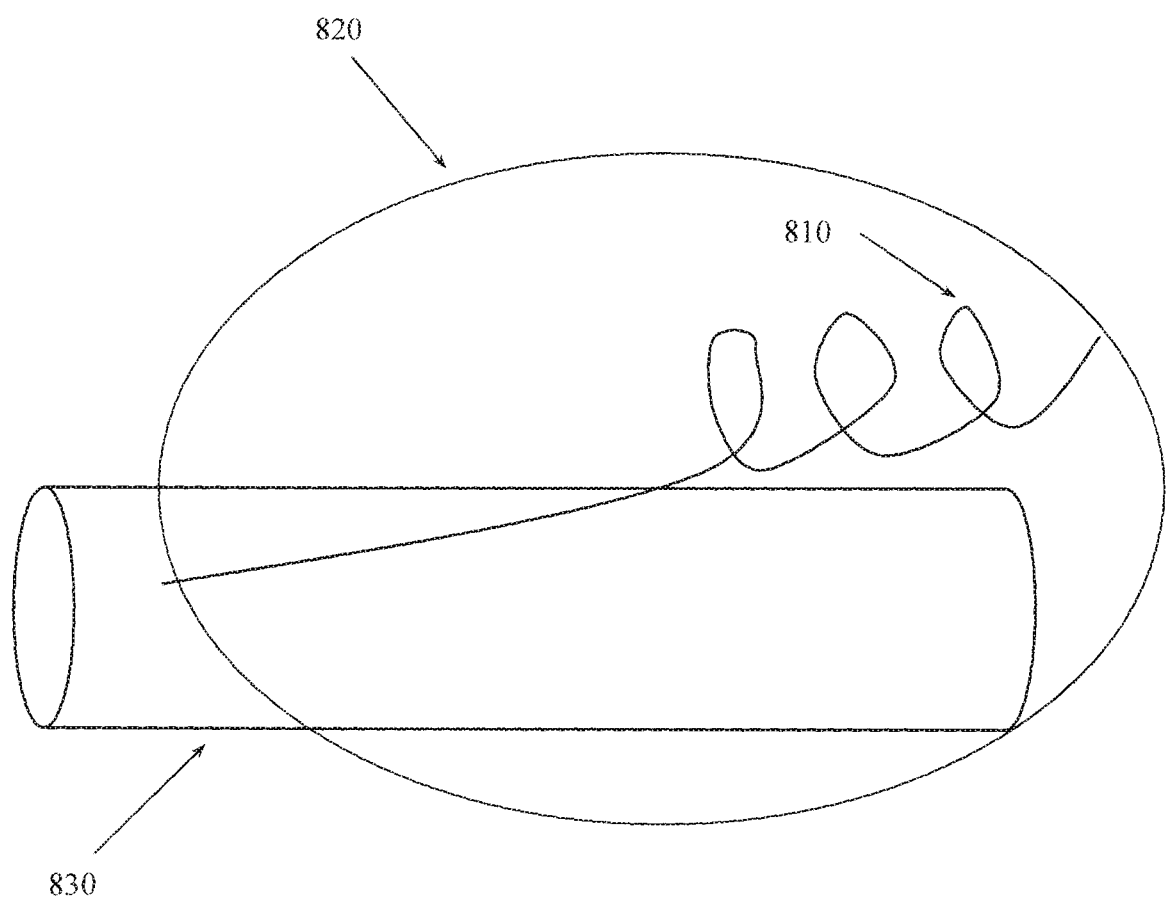
FIG. 8 illustrates an example targeted fascicular interface device with helical windings.

FIG. 8 illustrates an example targeted fascicular interface device 800. In one embodiment, a portion of the targeted fascicular interface device 800 may have helical windings 810 that add structural integrity to the fascicle/device interface 810. In one embodiment, the helical windings 810 may be positioned partially inside or partially outside the perineurium. In another embodiment, the helical windings 810 may be placed partially inside or partially outside the epineurium. Different embodiments may have different combinations of the positions of the helical windings 810. The helical windings 810 may end up partially in collagen 820 that has been applied or that has migrated to the entry/exit area where targeted fascicular interface device 800 entered the nerve 830. Adding structural integrity to the interface between the fascicle and the targeted fascicular interface device 800 facilitates improving or even optimizing stability at the interface with the nerve 830. Improving stability at the interface with nerve 830 mitigates micro motion issues in conventional systems that may have led to additional nerve damage.

Figure 9:
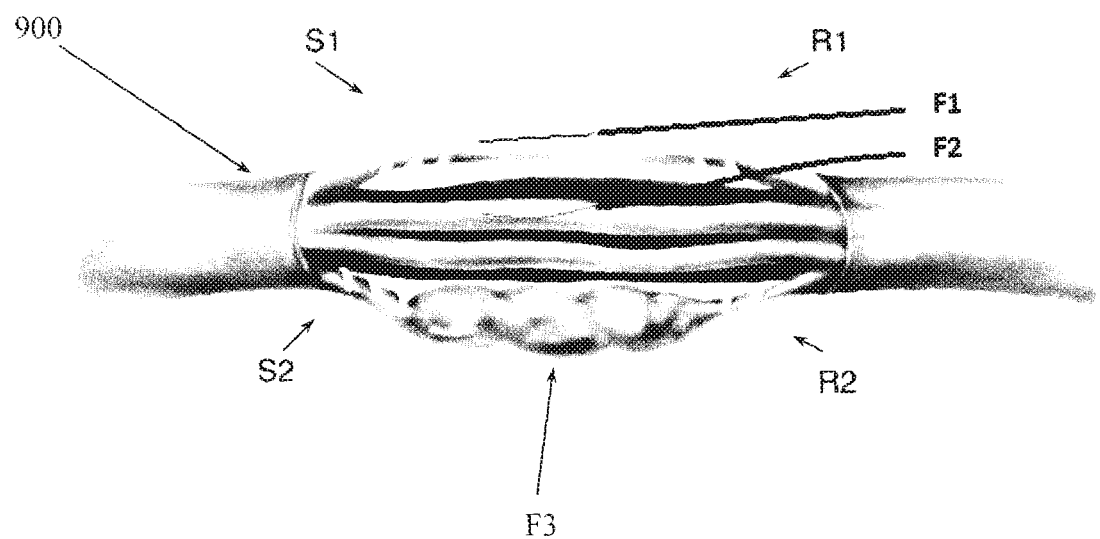
FIG. 9 illustrates a portion of a surgical practice for slit nerve repair.

A surgical procedure for implanting a micro-wire interface into a fascicle may include performing a split fascicle dissection. FIG. 9 illustrates a portion of a nerve undergoing slit nerve repair. The epineurium 900 is breached or removed and fascicles (e.g., F1, F2) in the nerve are exposed and separated. A stimulating hook electrode (e.g., S1, S2) is placed at one side of the exposed area and a recording electrode (e.g., R1, R2) is placed at the other side of the exposed area. The activation of S1 in a normal fascicle F1 generates a small but detectable compound action potential in R1. The activation of S2 in a damaged fascicle F3 generates no signal in R2, even though an action potential may have been present at S2. Conductors that are portions of a targeted fascicular interface device may then be placed in targeted fascicles based, for example, on the presence or absence of a naturally occurring or an induced action potential.

Figure 10:
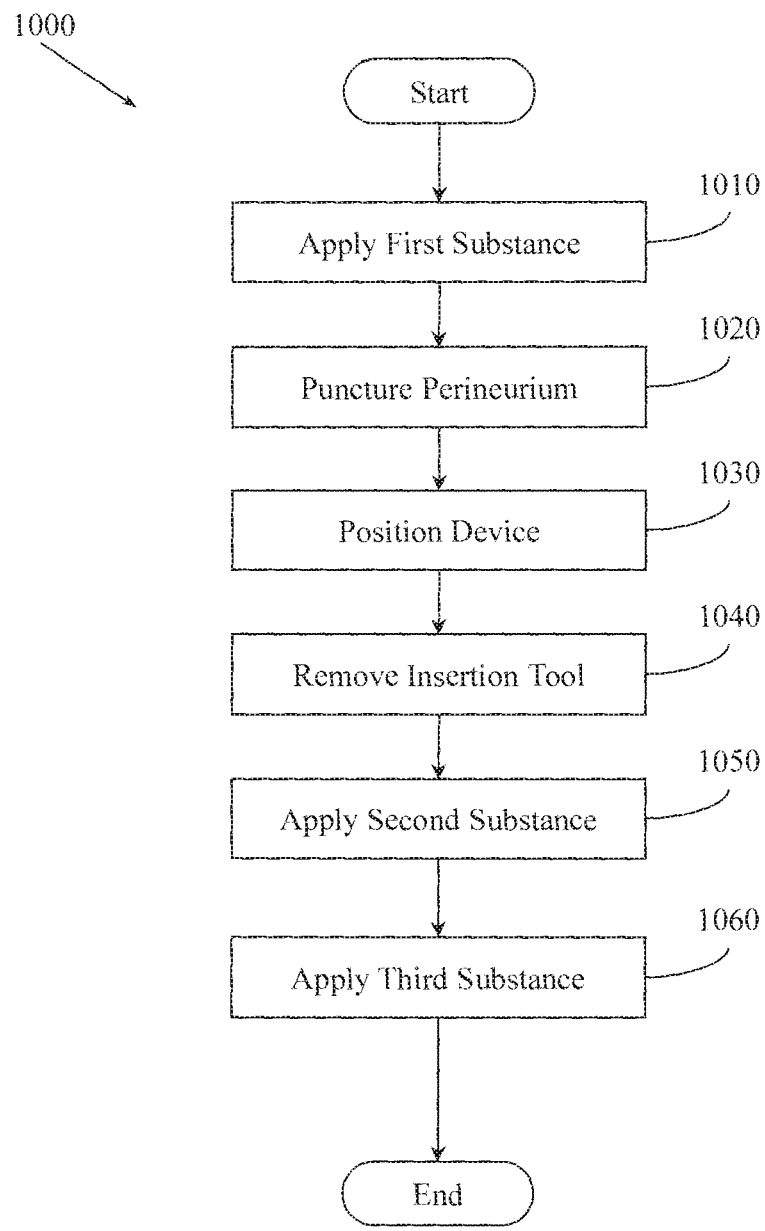
FIG. 10 illustrates a flow associated with an example surgical technique.

FIG. 10 illustrates a flow associated with one example surgical procedure 1000. The surgical procedure 1000 may include, at 1010, applying collagenase or another substance capable of breaking the bonds between collagen fibers to the epineurium of the nerve. Breaking bonds between collagen fibers may facilitate the dissection by splitting the bonds between collagen molecules in the epineurium. Once the epineurium has been sufficiently dissolved and the perineurium of a desired fascicle has been exposed, the nerve may be flushed to remove the collagenase or other dissolving substance. The flush may be performed using saline, for example.

Method 1000 may then proceed, at 1020, by puncturing the perineurium with an insertion tool to produce a single hole in the perineurium. The targeted fascicular interface device may then be inserted into the fascicle(s) with the insertion tool designed for the insertion procedure. Some conventional techniques produce two holes in the perineurium. Example apparatus and techniques may produce a single hole in the perineurium. Producing only a single hole in the perineurium while placing the targeted fascicular interface device facilitates minimizing damage that may occur during insertion.

At 1030, a portion of the targeted fascicular interface device may be positioned in the fascicle using the insertion tool using manual, electrostatic, magnetic, pneumatic, or other approaches. Once the targeted fascicular interface device has been placed, the insertion tool is removed at 1040 and fibrin sealant or another biocompatible, biodegradable substance that can contribute to holding the fascicle-device combination together is placed around the nerve to provide mechanical stability during the healing process. Over time, as fibroblasts invade the wound site, the sealant may be replaced by collagen or by fibroblasts. More generally, at 1050, a second substance is applied to the single hole in the perineurium to promote healing of the perineurium and to fix the device in place with respect to the fascicle. At 1060, a third substance is applied to the single hole in the epineurium to promote healing of the epineurium and to fix the device in place with respect to the nerve.

FIGS. 11-15 illustrate various embodiments of the insertion tool and an assembly of example insertion tools and example targeted fascicular interface devices. In one embodiment, the insertion tool may be tubular or round. In another embodiment, the insertion tool may not be tubular or round. In one embodiment, the insertion tool may have a channel, groove, trench, or other receiving portion into which a portion of the targeted fascicular interface device may be placed or affixed for insertion. The portion of the targeted fascicular interface device may be held in place on or in the insertion tool by, for example, winding the portion of the targeted fascicular interface device around the insertion tool. In one embodiment, the device may be wound at least two complete turns around the insertion tool. The targeted fascicular interface device may also be held in place on or in the insertion tool by affixing a portion of the targeted fascicular interface device to the insertion tool prior to insertion. The portion of the targeted fascicular interface device may be affixed to the insertion tool using a dissolvable or biodegradable sticky material (e.g., sucrose). The portion of the device may be affixed in the channel, groove, trench, or other receiving portion.

The insertion tool may have a sharp edge or point that penetrates the perineurium while producing less damage than conventional systems. For example, a conventional system may use a 35 gauge needle that pierces the perineurium at an entry site and an exit site. In one embodiment, the edge or point of the insertion tool may be designed to facilitate penetrating the perineurium at an acute angle with respect to the plane of the perineurium with an applied force of less than that required for a 35 gauge needle.

In one embodiment, the edge or point of the insertion tool used to puncture the perineurium may be less than 10 µm. In one embodiment, the edge or point of the insertion tool may be less than 3 µm. Using an insertion tool with these small dimensions facilitates minimizing damage that may occur during insertion.

Figure 11:
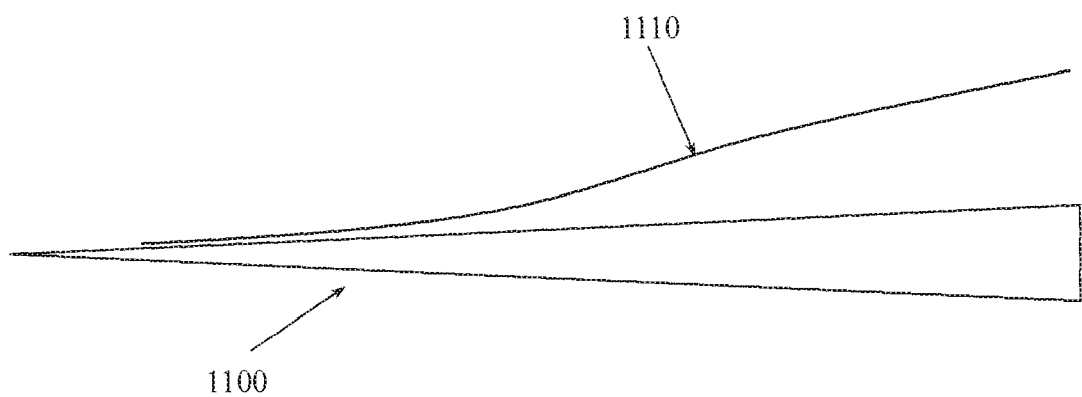
FIG. 11 illustrates an example insertion tool and targeted fascicular interface device assembly.
Figure 12:
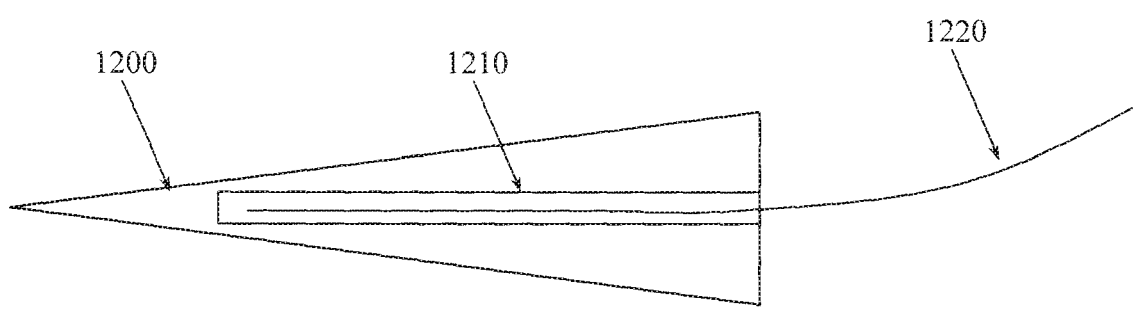
FIG. 12 illustrates an example insertion tool and targeted fascicular interface device assembly.
Figure 13:
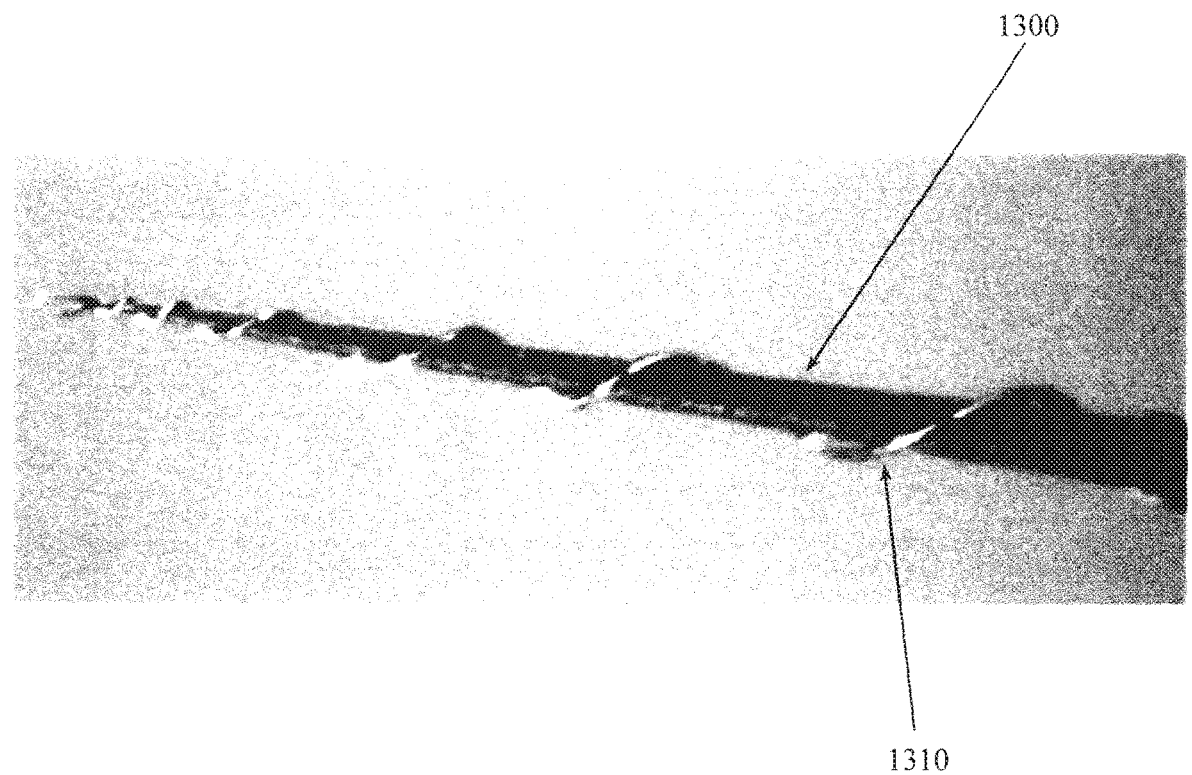
FIG. 13 illustrates an example insertion tool and targeted fascicular interface device assembly.
Figure 14:
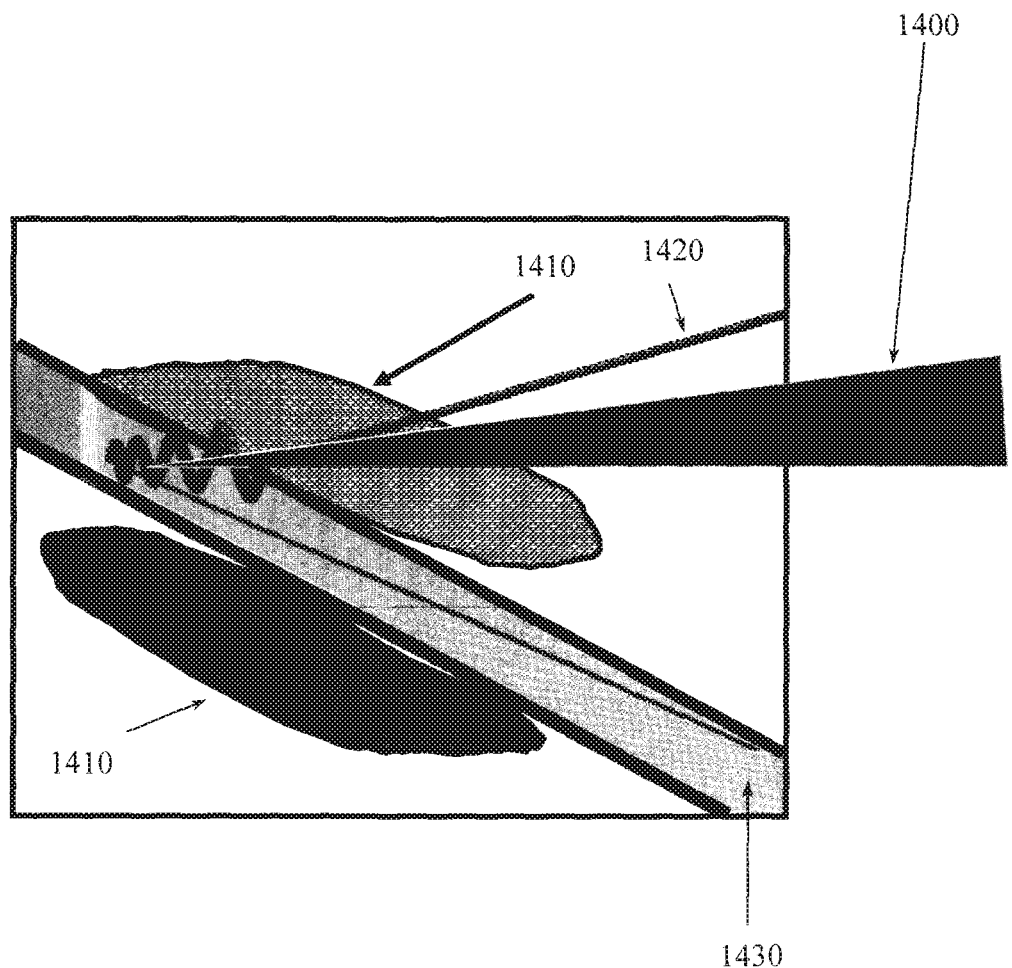
FIG. 14 illustrates an example insertion tool and targeted fascicular interface device assembly.
Figure 15:
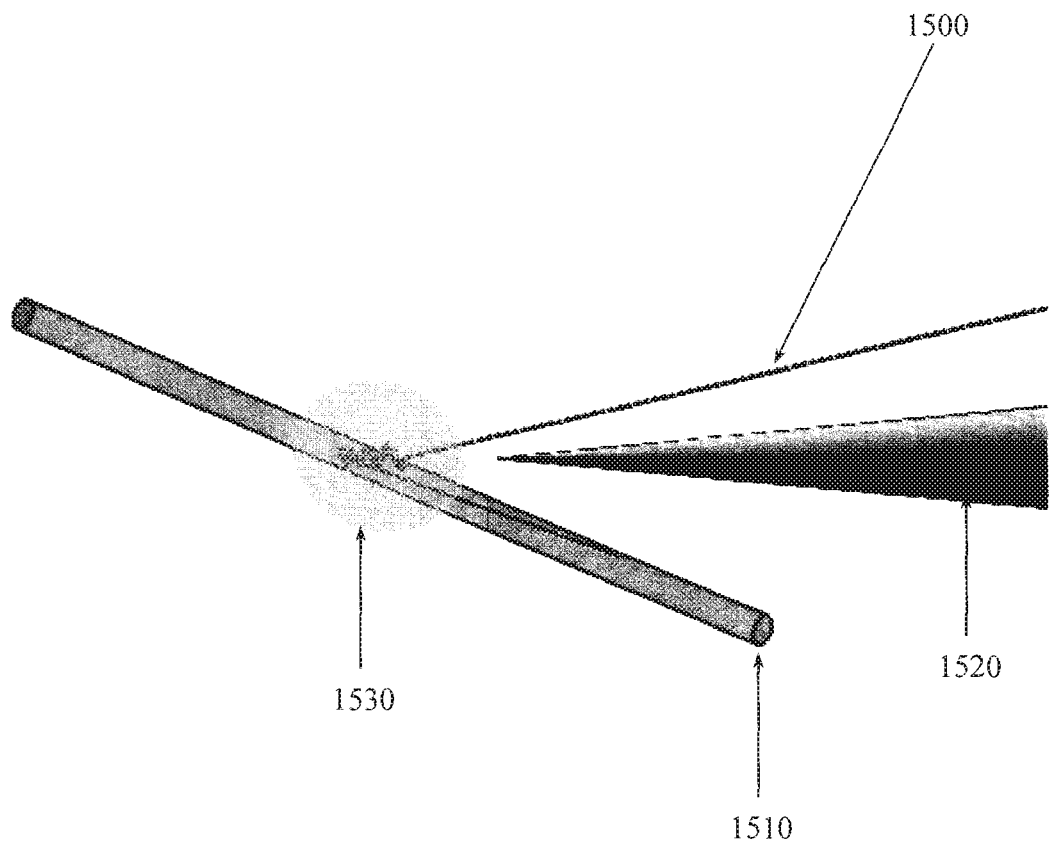
FIG. 15 illustrates an example insertion tool and targeted fascicular interface device assembly.

FIG. 11 illustrates an example insertion tool 1100 to which a portion of an example targeted fascicular interface device 1110 has been affixed. FIG. 12 illustrates an example insertion tool 1200 that has a groove 1210 into which a portion of an example targeted fascicular interface device 1220 has been affixed. FIG. 13 illustrates an example insertion tool 1300 around which a portion of an example targeted fascicular interface device 1310 has been wound. FIG. 14 illustrates an example insertion tool 1400 around which a portion of an example targeted fascicular interface device 1420 was wound. The insertion tool 1400 has penetrated fascicle 1430 and positioned device 1420. A substance 1410 has been placed around fascicle 1430 to promote healing at the site where tool 1400 penetrated fascicle 1430. Additionally and/or alternatively, the substance 1410 may also help fix device 1420 in place after the insertion tool 1400 is removed. FIG. 15 illustrates an example targeted fascicular interface device 1500 with a portion inserted into fascicle 1510. The insertion tool 1520 has been removed and substance 1530 has been placed around the fascicle 1510 to promote healing or to hold device 1500 in place with respect to fascicle 1510.

Once the targeted fascicular interface device has been sealed in place, the targeted fascicular interface device may be routed to a connector. The connector may be placed in a silicone electrode. The silicon electrode may be, for example, a cuff electrode that surrounds the nerve. The insertion, sealing, and routing may be repeated for other targeted fascicular interface devices placed in other fascicles.

Once all the desired targeted fascicular interface devices have been placed in the desired fascicles, the silicon electrode and wound site may be closed using conventional neurosurgical techniques. For example, epineurium originally removed to expose the fascicles may be placed back around the fascicles and devices and sown back into its original position.

In one embodiment, the targeted fascicle interface device may provide a communication channel for signals, data, or information received from within the fascicle. In one embodiment, the targeted fascicle interface device may provide a communication channel for signals, data, or information to be applied to the inside of the fascicle (e.g., for stimulating the fascicle). In one embodiment, the targeted fascicle interface device may include communication channels for both receiving and providing (e.g., recording and stimulating).

Example targeted fascicle interface devices may be placed to interface with different portions of the peripheral nervous system. For example, a targeted fascicular interface device may be placed to interface with spinal dorsal roots, or with spinal ventral roots. In different embodiments, the targeted fascicular interface device may be applied to nerves that contain a single fascicle or to nerves that contain two or more (e.g., 5, 10, 20) fascicles. The targeted fascicular interface device may be applied to nerves that are located different distances from the spinal cord and within the dorsal or ventral roots. In different embodiments, the targeted fascicular interface device may be applied to sensory fascicles, motor fascicles, proprioceptive fascicles, sympathetic fascicles, parasympathetic fascicles, or other fascicles.

The targeted fascicular interface device may be used for different types of systems. For example, the targeted fascicular interface device may be used in an open loop system for recording from fascicles, for an open loop system for stimulating fascicles, to provide motor signals to drive an artificial limb or other prosthetic, to facilitate restoring sensation in patients with amputated limbs or other anatomical compromises, or in other ways.

The targeted fascicular interface device may also be used in closed loop systems. For example, the targeted fascicular interface device may be used to record signals for satiety from the gastric nerve, to apply a signal to induce nausea in patients with obesity by placing electrodes in the vagus nerve fascicles, or to produce other sensations or results in response to detecting other signals.

In one embodiment, the targeted fascicular interface device may be used as a surgical tool. For example, the targeted fascicular interface device may be used to monitor fascicle viability before surgical resection or repair. The monitoring capability may also be employed to facilitate monitoring the health or disease state of an organ innervated by the peripheral nervous system. For example, a first set of signals may be associated with a healthy organ while a second, different set of signals may be associated with a diseased organ such as the heart, spleen or liver. More generally, the targeted fascicular interface device may be used to monitor state, conditions, or events associated with a particular fascicle in the PNS, or even with a single axon in the PNS.

While monitoring facilitates identifying a state, condition, or event from signals acquired from a fascicle or axon through the targeted fascicular interface device, stimulation facilitates sending desired signals through a nerve. Stimulation may, therefore, facilitate restoring or improving a function of a body part that is innervated by the peripheral nervous system. More generally, the targeted fascicular interface device may be used to influence a state, condition, or event associated with a particular fascicle in the peripheral nervous system by stimulating the particular fascicle.

Example apparatus and methods have been examined using the sciatic nerve in a rat model. In the rat model, the sciatic nerve is easy to access and has a varying number (e.g., 4, 5) of fascicles ranging from 200 to 600 μm in diameter. The rat sciatic nerve is routinely used as a training model for neurosurgeons practicing fascicular repair. The sciatic nerve may be dissected in the popliteal fossa just above the knee. A stimulation electrode and recording electrode proximal and distal to the site of insertion respectively may be placed using a surgical procedure similar to that for split fascicle repair.

In the rat model, electromyography (EMG) electrodes are placed in the medial gastrocnemius and tibialis anterior. Collagenase type II from Sigma may be injected within the epineurium. Collagenase type II is an enzyme capable of breaking the bonds between the collagen molecule. Different concentrations of collagenase may be used in different applications. For example, concentrations of 300 units/ml and 600 units/ml may be employed. The collagenase reaction may be cleared by applying saline to the site where the solution was applied. A 10 μm diameter wire with polyurethane insulation may be placed underneath the perineurium using the insertion tool. Fibrin sealant may then be applied to maintain the relative position of the electrode and fascicles. The rat model demonstrates that a microwire can be placed within the fascicle with negligible effect on the compound action potential while providing a high (e.g., >5) signal to noise ratio.

In one embodiment, an implantable electronics package may be provided to interface with micro-wires or nano-wires implanted within fascicles. The implantable electronics package may be located close to the nerve (e.g., <5 mm). In one embodiment, the implantable electronics package may include electronic components including, but not limited to, amplifiers, A/D converters, stimulators and multiplexors. Placing electronic components in the implantable electronics package may reduce the numbers of wires that enter and exit the body. Additionally, placing electronic components in the implantable electronics component may reduce or even minimize noise. In one embodiment, an amplifier may be added to the targeted fascicular interface device. The amplifier may be electrically connected to the conductor of the device. In one embodiment, the combination of the conductor and the amplifier provide a signal with a signal to noise ratio (SNR) of less than 2 μV RMS. In one embodiment, the combination of the conductor and the amplifier have an input impedance greater than 20 MΩ, provide a signal with a bandwidth of 800 Hz to 6 kHz, provide a signal with a dynamic voltage range of 0-1 mV, and provide a signal with an amplitude of 0-1 mA.

In one embodiment, the implantable electronics package may be hermetically sealed. The implantable electronics package may be, for example, 1 cm×1 cm×5 mm. Other dimensions may be employed. In one example, the implantable electronics package may be configured to communicate with the outside through percutaneous wires.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the embodiments described herein. Therefore, the invention is not limited to the specific details, the representative apparatus, and illustrative examples shown and described. Thus, this application is intended to embrace alterations, modifications, and variations that fall within the scope of the appended claims.

References to "one embodiment", "an embodiment", "one example", "an example", and other similar exemplary language indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

What is claimed is:

1. A method for implanting a device for interfacing with an axon inside a single fascicle in a nerve in the peripheral nervous system (PNS) via a single hole in the epineurium of the nerve and a single hole in the perineurium of the fascicle, the method comprising:
mechanically or chemically attaching a portion of the device to an insertion tool;
applying a first substance to at least partially dissolve the epineurium to at least partially expose the perineurium;
puncturing the perineurium with the insertion tool to produce the single hole in the perineurium;
visually guiding the device through the single hole in the epineurium and the single hole in the perineurium using the insertion tool into a position so that a conducting portion of the device is located longitudinally in the fascicle and so that an insulating portion of the device is in contact with an edge of the single hole in the perineurium;
removing the insertion tool to leave the device at the position;
applying a second substance to the single hole in the perineurium to promote healing of the perineurium and to fix the device in place with respect to the fascicle, and
applying a third substance to the single hole in the epineurium to promote healing of the epineurium and to fix the device in place with respect to the nerve.

2. The method of claim 1, wherein the first substance is collagenase.

3. The method of claim 1, wherein the second substance is a fibrin sealant.

4. The method of claim 3, wherein the third substance is a fibroblast growth factor.

5. The method of claim 1, wherein the device is placed within 200 μm of a targeted axon.

6. The method of claim 1, further comprising:
testing the position of the device with respect to the axon by stimulation or recording, and
repositioning the device until a desired positioning with respect to the axon is achieved.

7. The method of claim 1, wherein
the conducting portion of the device comprises a wire that is biocompatible having a geometry that includes a diameter of less than 11 μm and a length, wherein the wire is selected to have a flexural rigidity measure matching a flexural rigidity of the single fascicle; and
the insulating portion of the device comprises an insulator that covers a portion of the wire.

8. The method of claim 7, wherein the insulator comprises a material that adheres to the perineurium.

9. The method of claim 8, wherein the insertion tool is shaped and sized to create the single hole in the perineurium and to deliver the device to the inside of the fascicle through the single hole in the perineurium,
wherein a tip of the insertion tool that creates the single hole in the perineurium is less than 5 μm in diameter, and
wherein the insertion tool is shaped and sized to penetrate the perineurium surrounding the axon.

10. The method of claim 7, wherein the length is 5 mm.

11. The method of claim 7, wherein the wire comprises carbon nanotubes.

12. The method of claim 7, wherein the wire is configured to be connected to a recording device to record an electrical signal from the axon within the fascicle of the nerve or configured to be connected to a stimulator device to provide an electrical stimulation to the axon within the fascicle of the nerve.

* * * * *